US008702676B2

(12) United States Patent
Hauschild et al.

(10) Patent No.: US 8,702,676 B2
(45) Date of Patent: Apr. 22, 2014

(54) SURGICAL INSTRUMENT FOR INJECTING A DRUG INTO PROSTATE TISSUE

(71) Applicant: AMS Research Corporation, Minnetonka, MN (US)

(72) Inventors: Sidney F. Hauschild, Brooklyn Park, MN (US); Stephen L. Bolea, Watertown, MN (US); Johann J. Neisz, Coon Rapids, MN (US)

(73) Assignee: AMS Research Corporation, Minnetonka, MN (US)

( * ) Notice: Subject to any disclaimer, the term of this patent is extended or adjusted under 35 U.S.C. 154(b) by 0 days.

(21) Appl. No.: 13/757,212

(22) Filed: Feb. 1, 2013

(65) Prior Publication Data

US 2013/0144265 A1 Jun. 6, 2013

Related U.S. Application Data

(60) Division of application No. 13/547,479, filed on Jul. 12, 2012, which is a continuation of application No. 11/148,095, filed on Jun. 8, 2005, which is a division of application No. 10/269,405, filed on Oct. 11, 2002, now Pat. No. 6,905,475.

(60) Provisional application No. 60/329,262, filed on Oct. 12, 2001.

(51) Int. Cl.
*A61M 31/00* (2006.01)

(52) U.S. Cl.
USPC .......................... 604/500; 604/509; 604/264

(58) Field of Classification Search
USPC .................. 604/264, 6.06, 500, 509, 508
See application file for complete search history.

(56) References Cited

U.S. PATENT DOCUMENTS

| | | | |
|---|---|---|---|
| 4,461,283 | A | 7/1984 | Doi |
| 4,674,501 | A | 6/1987 | Greenberg |
| 4,892,244 | A | 1/1990 | Fox et al. |
| 5,031,814 | A | 7/1991 | Tompkins et al. |
| 5,156,315 | A | 10/1992 | Green et al. |
| 5,292,330 | A | 3/1994 | Shutt |

(Continued)

FOREIGN PATENT DOCUMENTS

| | | |
|---|---|---|
| WO | WO 92/10142 | 6/1992 |
| WO | WO 93/15664 | 8/1993 |
| WO | WO 03/005889 | 1/2003 |

OTHER PUBLICATIONS

DiTrolio, J.V., *Transurethral Ablation of the Prostate*, presented at the American Urological Association 94th Annual Meeting (Mar. 1999).

(Continued)

*Primary Examiner* — Kevin C Sirmons
*Assistant Examiner* — Edelmira Bosques
(74) *Attorney, Agent, or Firm* — Kagan Binder, PLLC

(57) ABSTRACT

Method and surgical instrument for treating prostate tissue including a surgical instrument having a main body, a needle deployment port, a needle, first and second handles and a lockout release mechanism to limit needle extension. Additionally, a kit includes the surgical instrument, together with a cystoscope, and optionally a syringe and reservoir of ethanol. The method includes needle-less injection and visualizing the ethanol injection by delivering both an echogenic agent and ethanol either by needle or needle-less injection or by providing an ultrasonically visible marker near the tip of the ethanol delivery cannula. The method also includes extending the needle transversely of the instrument housing using a link assembly.

10 Claims, 21 Drawing Sheets

(56) References Cited

U.S. PATENT DOCUMENTS

| | | |
|---|---|---|
| 5,306,284 A | 4/1994 | Agee et al. |
| 5,322,503 A | 6/1994 | Desai |
| 5,542,948 A | 8/1996 | Weaver et al. |
| 5,562,703 A | 10/1996 | Desai |
| 5,630,794 A | 5/1997 | Lax et al. |
| 5,672,171 A | 9/1997 | Andrus et al. |
| 5,861,002 A | 1/1999 | Desai |
| 6,033,404 A | 3/2000 | Melzer et al. |
| 6,231,591 B1 | 5/2001 | Desai |
| 6,461,296 B1 | 10/2002 | Desai |
| 6,699,214 B2 | 3/2004 | Gellman |
| 6,905,475 B2 | 6/2005 | Hauschild et al. |
| 6,905,480 B2 | 6/2005 | McGuckin, Jr. et al. |
| 2002/0120238 A1 | 8/2002 | McGuckin, Jr. et al. |
| 2002/0143302 A1 | 10/2002 | Hinchliffe et al. |
| 2003/0073908 A1 | 4/2003 | Desai |
| 2003/0130575 A1 | 7/2003 | Desai |
| 2004/0002647 A1 | 1/2004 | Desai |

OTHER PUBLICATIONS

DiTrolio, J.V., *Chemoablation of the Prostate with Dehydrated Ethanol for Treatment of BPH*, 5th Int'l Consultation on BPH, 1 page (Jun. 2000).

Prostaject Ethanol Injection System Brochure, American Medical Systems (Mar. 1999).

Abstracts, British Journal Urology, V86 (suppl 3), 1 page (Nov. 2000).

Abstracts, Journal Endourology, V16 (suppl 1), 1 page (Sep. 2002).

Haupt, Gerald et al., New Way to Delivery Fluids: Endoscopic Jet Injection Into the Beagle Prostate, The Journal of Urology, vol. 170, pp. 2097-2100 (Nov. 2003).

Watson, Richard A. et al., Transurethral Ethanol Ablation of the Prostate, Abstract, The Journal of Ur9ology, vol. 161, No. 4 (suppl).

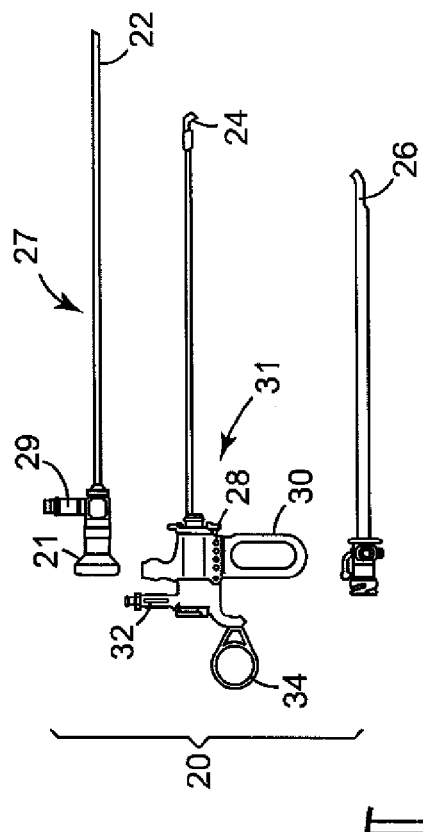
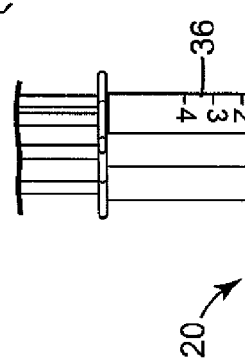
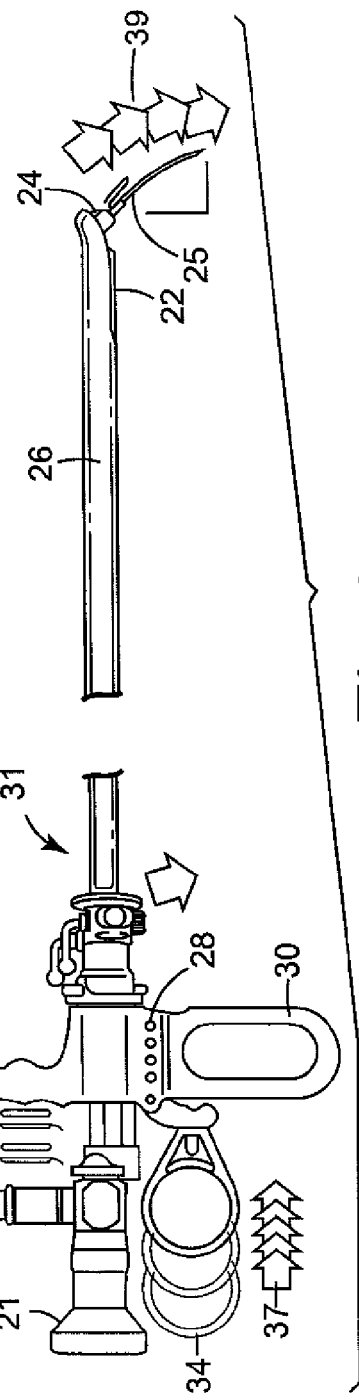
Fig. 2
Fig. 3

SURGICAL INSTRUMENT FOR INJECTING A DRUG INTO PROSTATE TISSUE

CROSS REFERENCE TO RELATED APPLICATION

This application is a divisional application of U.S. application Ser. No. 13/547,479, filed Jul 12, 2012, which is a continuation application of U.S. application Ser. No. 11/148,095, filed Jun. 8, 2005, which is a divisional application of U.S. application Ser. No. 10/269,405, now U.S. Pat. No. 6,905,475, which claims the benefit of U.S. provisional patent application Ser. No. 60/329,262, filed Oct. 12, 2001, all of which are hereby incorporated by reference in their entireties.

BACKGROUND OF THE INVENTION

The present invention relates to surgical instruments and methods, particularly those for treating prostate tissue, and to surgical kits for use in such methods.

FIG. 1 illustrates the anatomical position of the prostate 10 (including lateral lobes 15) and adjacent tissue including the seminal vesicles 11, bladder neck 12, and pelvic tissues including sphincter muscles 14.

Prostate disease is a significant health risk for males. Diseases of the prostate include prostatitis, benign prostatic hyperplasia or hypertrophy (BPH) and prostatic carcinoma. Benign prostatic hypertrophy is a very common disorder, affecting an estimated 12 million men in the United States alone. BPH is a chronic condition and is strongly age related; approximately 50% of men over 50, 75% of men over the age of 70 and 90% of men over the age of 80 have BPH.

BPH is treated with a large number of therapeutic modalities. Transurethral resection of the prostate (TURP) is a preferred method of treating BPH. A typical TURP involves general anesthesia, and the placement of a resectoscope in the urethra to remove multiple small chips of hyperplastic prostatic tissue, thereby relieving the obstruction by removing the adenoma. Complications from TURP include bleeding, incontinence, retrograde ejaculation and impotence.

Examples of surgical devices for prostate tissue treatment are disclosed in U.S. Pat. Nos. 4,461,283; 5,672,171 and 5,630,794 and PCT International Publication Nos. WO 92/10142 and WO 93/15664 (the entire contents of each of which are herein incorporated by reference). Examples of invasive techniques that surgically damage prostate tissue include laser treatments (including side firing, contact and interstitial laser procedures), and transurethral ethanol ablation of the prostate (TEAP) as described in DiTrolio, J. V., *Transurethral Ablation of the Prostate*, presented at the American Urological Association 94th Annual Meeting, March 1999; and DiTrolio, J. V., *Chemoablation of the Prostate with Dehydrated Ethanol for Treatment of BPH*, 5th International Consultation on BPH, June 2000 in Paris, France (the entire contents of each of which are herein incorporated by reference). Examples of devices and methods for surgically damaging prostate tissue are disclosed in U.S. Pat. Nos. 5,322,503; 5,562,703; 5,861,002; 6,231,591 and 6,461,296.

BRIEF DESCRIPTION OF THE DRAWINGS

FIG. 2 is a side view of a disassembled surgical instrument for use in a preferred embodiment of the present invention.

FIG. 3 is an enlarged side view of the surgical instrument of FIG. 2 in an assembled condition, that uses arrows to show the motion of elements of the surgical instrument during deployment of a needle.

FIG. 12b is an enlarged view of a portion of FIG. 12a.

FIG. 13c is a perspective view corresponding to FIG. 13a.

FIG. 18b is a detailed section view of a portion of FIG. 18a.

FIG. 19b is a plan view of the locking mechanism of FIG. 19a.

DETAILED DESCRIPTION

Figure 1:
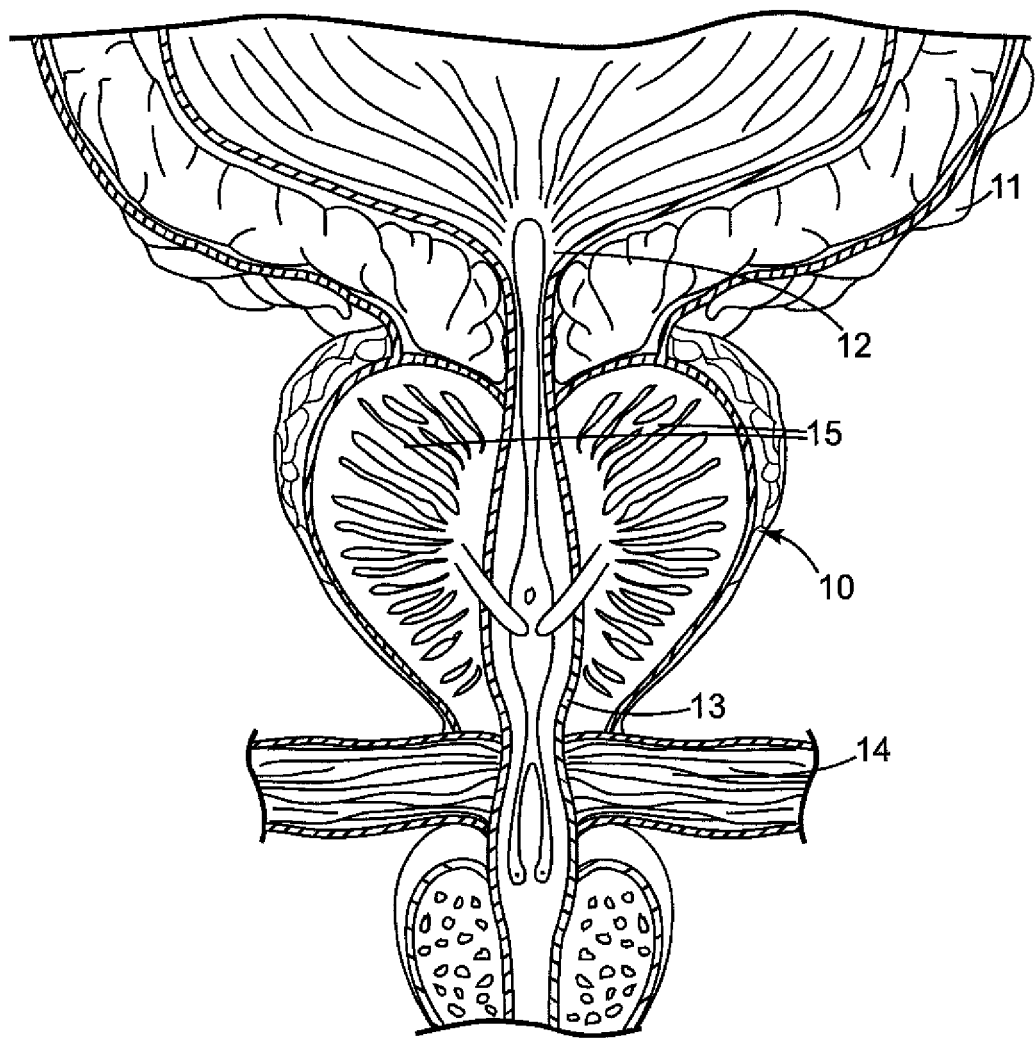
FIG. 1 is a schematic side view showing the anatomical location of prostate tissue.

FIGS. 2 and 3 show a preferred embodiment of surgical instrument 20 for use in treating prostate tissue by injecting an effective amount of an active ingredient (e.g. ethanol, acetic acid, phenol, Lidocaine, bulking agents, botox, oxybutenin, carboxylic acid). FIG. 2 shows the device 20 in an unassembled condition and FIG. 3 shows the device 20 in an assembled condition.

The device 20 includes a scope sheath 22 with eye port 21, a sheath 26 and a main body with a needle deployment port 24, handle 30 and thumb ring 34. The main body also includes an ethanol syringe port 32 that is designed to mate with a syringe 86. Preferably the syringe 86 has a threaded-Luer Lok® connector, as opposed to a bayonet syringe or a non-threaded Luer-Lok® connector. (Luer-Lok® is a registered trademark of Becton, Dickinson and Company.) Detents 28 are provided for precise needle advancement through auditory, visual and tactile confirmation of needle-tip position in a lobe of the prostate.

The surgical device 20 is preferably sized and shaped for transurethral entry under direct vision. Optionally, a conventional cystoscope 27 and sheath 26 for transurethral entry under direct vision may be utilized as a portion of a kit 40. Alternatively, the device may be sized and shaped for transrectal use. It is to be understood that kit 40 preferably includes device 20, syringe 86 and needle 76, and optionally includes a reservoir 72 of ethanol or other therapeutically effective agent.

The assembled device 20 is advanced into the prostatic urethra. The scope allows visual positioning of the needle port against the urethra adjacent to the lobe of the prostate to be treated. The needle is advanced (as shown in the arrows in FIG. 3) one detent click at a time (e.g. 0.5 cm) to place the needle tip in the adenoma. A small volume (e.g. 3 to 5 ml) of an active ingredient such as anhydrous alcohol (ethanol) is slowly injected into the tissue. The urethral lumen may be continuously irrigated while the ethanol is being administered.

The needle may then be withdrawn and the device 20 is removed from the sheath. The system may be rotated to target the next transurethral access point. An injection may be made to each lateral lobe of the prostate and in cases with median lobe enlargement, an injection may be made to the median lobe of the prostate. In cases of longer prostatic urethra, a second plane of injections may optional be administered. For example, a total amount of about 13 ml may be the average amount of ethanol injected per patient.

The total dosage of ethanol will depend on a variety of factors including, but not limited to the size of the prostate, the shape of the prostate (e.g. length and width), the number of injection sites determined, and the nature and degree of prostate disease. The amount of ethanol could range from one or two mls to about 20 mls or more.

Optionally, the method may include other steps commensurate with the physician's treatment strategy. Also optionally, other therapeutically effective agents may be used with the surgical devices according to the present invention, including the substances described in U.S. patent application Ser. No. 10/193,716, filed Jul. 9, 2002 with the title REGIMEN FOR TREATING PROSTATE TISSUE AND SURGICAL KIT FOR USE IN THE REGIMEN, now U.S. Pat. No. 7,015,253, issued Mar. 21, 2006,the entire contents of which are hereby incorporated by reference.

In another embodiment, the ethanol may be combined with another agent that enhances delivery and distribution of the ethanol within the prostate tissue. More preferably, the agent may more effectively disperse the ethanol in the vasculature of the prostate tissue. For example, the ethanol may be combined with GELFOAM® Sterile Powder, available from Pharmacia & Upjohn of Kalamazoo, Mich. The GELFOAM powder is believed to enhance the retention of the ethanol within the prostate tissue and to more effectively deliver the ethanol to the capillaries associated with the prostate tissue. Alternatively, the ethanol may be combined with a means for enhancing visualization of the ethanol. For example, the agent may comprise a dye for enhancing visualization of the ethanol. Better visualization of the ethanol may assist some surgeons in more effectively delivering the ethanol to the prostate tissue and avoiding undesirable backflow.

In a preferred embodiment, the needle deployment port 24 is designed to afford a complete view of the entire needle at all points of deployment.

Figure 4:
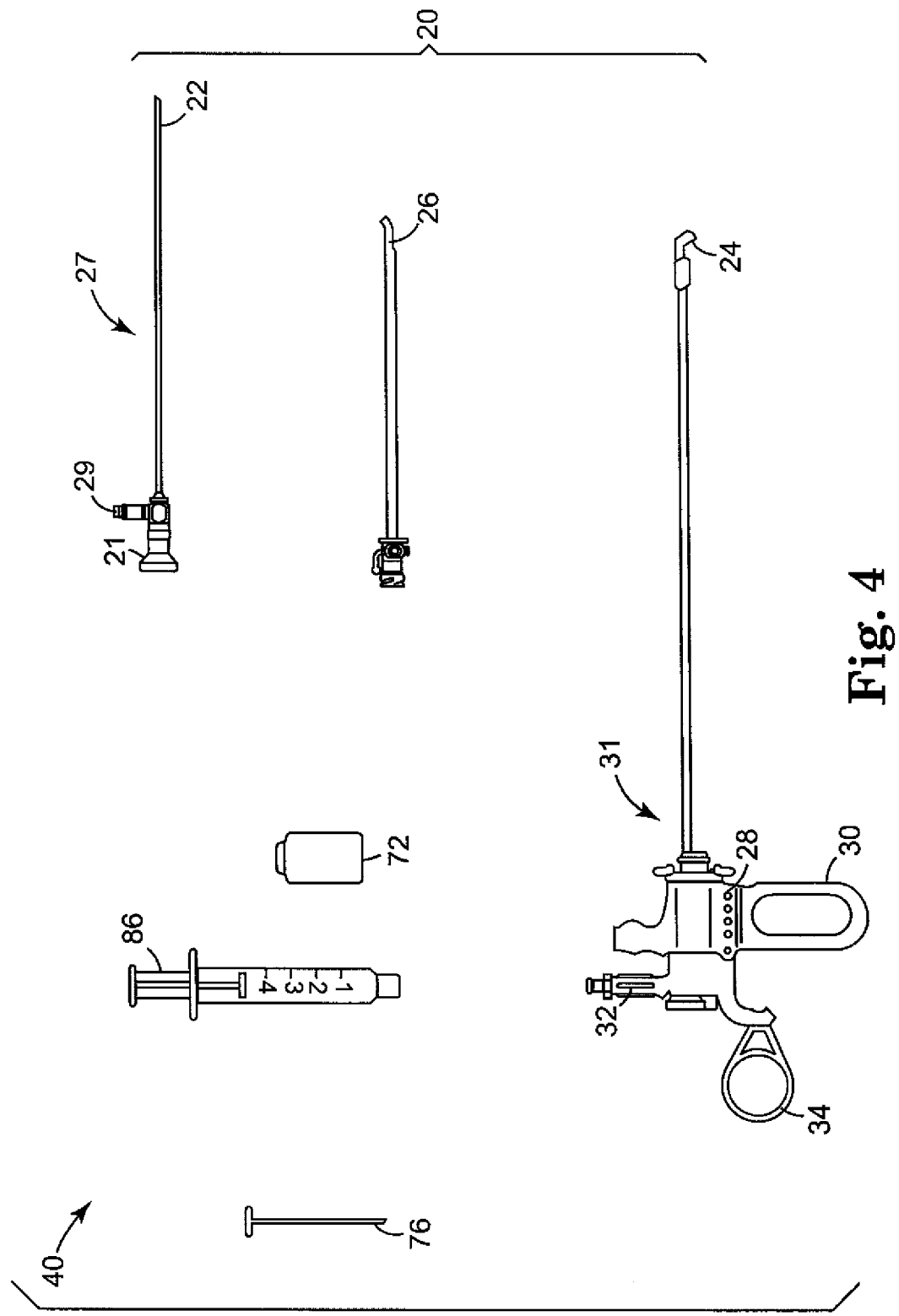
FIG. 4 is a side view showing a surgical kit according to another aspect of the present invention.

In another aspect, the present invention comprises the kit 40 for treating a human male. The kit 40 may comprise a surgical kit. FIG. 4 illustrates one example of a surgical kit 40 according to the present invention. The kit 40 includes a surgical device for damaging, treating or therapeutically affecting prostate tissue according to the present invention.

The kit 40 includes the surgical device 20 described in conjunction with FIGS. 2 and 3. The device 20 includes a cystoscope 27 having a scope sheath 22 with eye port 21, a sheath 26 and a light cord connector 29. Device 20 also includes main body 31 with a needle deployment port 24, needle 25, handle 30 and thumb ring 34. The main body 31 also includes an ethanol syringe port 32 with a threaded Luer-Lok® feature. Detents 28 are also provided.

Notably, the present invention is suitable for use in two piece assemblies in contrast to the three piece assembly shown in FIG. 2. For example, the function of the sheath 26 and main body 31 could be combined into a unitary piece that is designed to operate in conjunction with endoscope 27. Also notably, the assembly may comprise a rigid assembly with, for example, a rigid sheath 26 and scope 27. Alternatively, the present invention includes embodiments that include flexible assemblies, including, for example, flexible scopes 27 and flexible sheaths 26.

The kit 40 also includes a supply or reservoir 72 of a therapeutically effective substance such as ethanol or a bulking agent. Needle 76 and syringe 86 are provided to load the ethanol into syringe 86 from reservoir 72. The syringe 86 may then be used to deliver ethanol 72 through the needle 25 during a surgical procedure. Preferably, the delivery is transurethrally. In operation, thumb ring 34 and handle 30 are manually grasped and drawn together in the direction indicated by arrow 37, causing needle 25 to advance in the direction of arrow 39. It is to be understood that the detents 28 may be used to stop advancement of needle 25 at predetermined distances set by the location of the individual elements of the detents 28. Once the needle 25 is advanced to the desired position within the prostate 10, syringe 86 is operated to deliver ethanol via needle 25 to the prostate 10, as desired. When delivery of ethanol is complete, thumb ring 34 is manually fully retracted away from handle 30 in a direction opposite to arrow 37, causing needle 25 to retract into the needle deployment port 24 in a direction opposite to arrow 39.

In another embodiment, the thumb ring 34 may be biased toward the position where the needle is fully retracted.

The elements of the kit may be packaged and sterilized together, or they may be separately packaged and sterilized and assembled into a kit at a later date.

Figure 5:
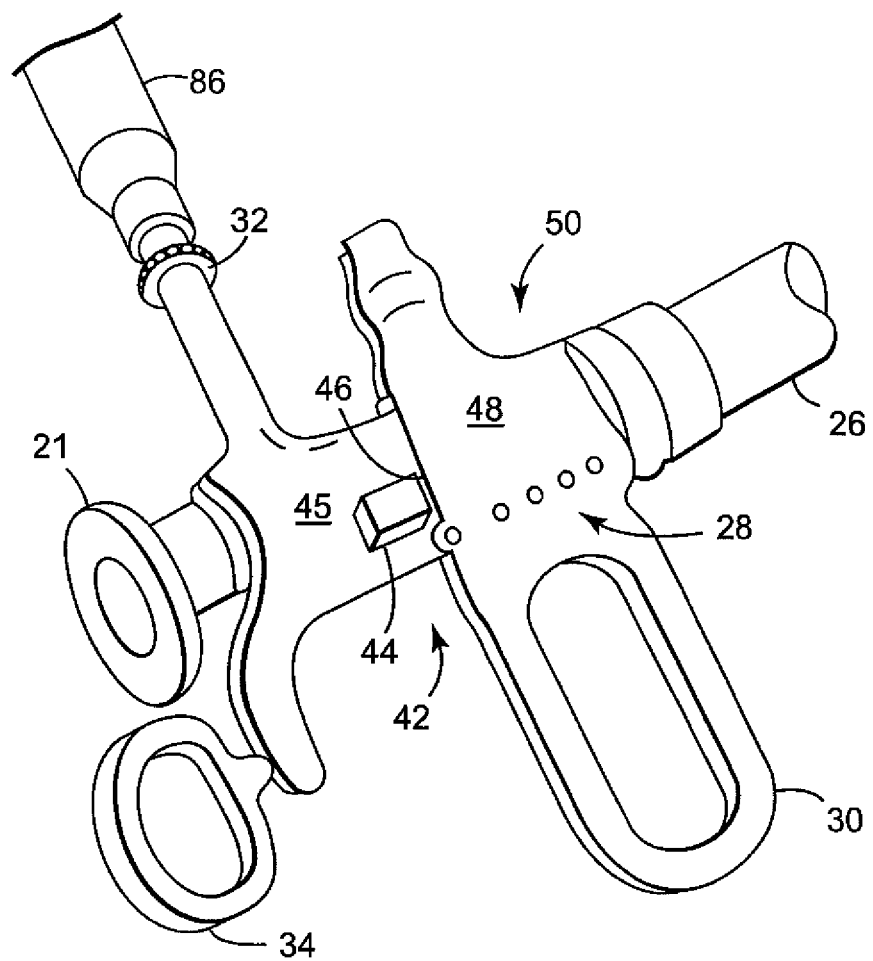
FIG. 5 is a view of another variation of the surgical instrument according to the present invention.

Referring to FIG. 5, a lockout release 42 can be added to the surgical instrument of FIGS. 2-4 to prevent premature deployment of the needle 25. The lockout release 42 can be a button 44 which is spring loaded and will automatically re-lock when the needle is retracted. When button 44 is in the position shown in FIG. 5, button 44 will prevent advancement of the needle 25 via movement of a slide 45 because of interference with edge 46 of a frame 48 of the handle or finger grip 30 of a modified Prostaject device 50. (Prostaject devices are available from American Medical Systems, Inc. of Minnetonka, Minn., U.S.A..) There are a number of possible ways to implement the concept, all involving the means to prevent or inhibit the relative motion between the handle/cystoscope and the slide/needle. The means to prevent or inhibit this movement can be removed by actuating a button when the physician is ready to advance the needle. The button will re-set when the needle is retracted. Because the force needed to insert the device transurethrally is in the same direction as the force needed to advance the needle 25, there is a chance that the needle 25 can be prematurely deployed, causing a hazard to the patient. This device (the lockout release 42) will prevent this from happening. There are a variety of ways of implementing this concept, but all result in a structure that prevents or inhibits movement of the slide 45 relative to the front handle 30 and frame 48.

Figure 16A:
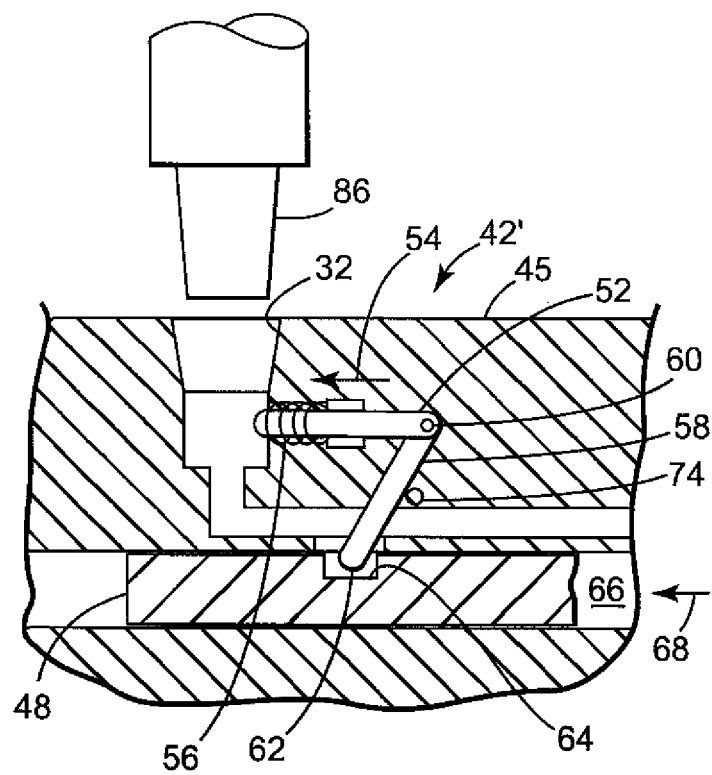
FIG. 16a is a view of a lockout arrangement according to an aspect of the present invention in a first, locked, position.
Figure 16B:
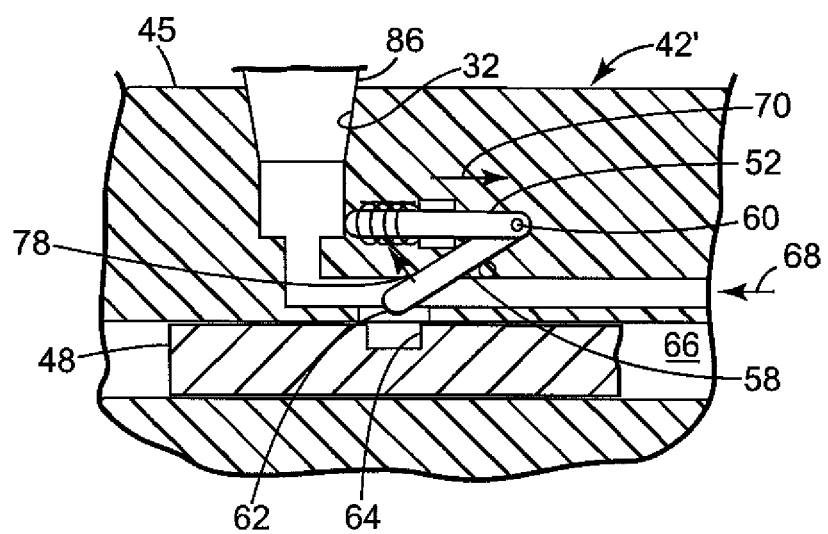
FIG. 16b is a view of the lockout arrangement of FIG. 16a in a second, unlocked, position.

In another embodiment, a lockout assembly may be added to ethanol syringe port 32 that prevents or inhibits advancement of the needle (by advancing thumb ring 34) without a syringe 86 inserted in the syringe port 32. FIGS. 16a and 16b schematically illustrate a lockout release or assembly 42' in both the locking and release positions. Although not shown in FIGS. 16a and 16b, it is to be understood that syringe 86 is a Luer-Lok® type syringe. In FIG. 16a, the lockout assembly 42' is shown in a blocking position where a first lockout arm or member 52 is urged in the direction of arrow 54 by a spring 56 acting against slide 45. A second lockout arm or member 58 is connected to the first lockout arm 52 at a pivot 60. A distal end 62 of member 58 engages a blocking topology or notch 64 in an actuation member 66 which is operatively associated with the frame 48 and finger grip 30. In FIG. 16a it may be seen that slide 45 is blocked (i.e., in a blocking condition) from advancing in the direction of arrow 68 by the interengagement of end 62 and notch 64. In FIG. 16b, a release position or condition may be seen in which the syringe 86 urges first member 52 in the direction of arrow 70 acting against spring 56 and causing member 58 to pivot against a fixed point or fulcrum 74 in slide 45, moving in the direction of arrow 78 to move distal end 62 out of engagement with member 66, allowing movement of slide 45 in the direction of arrow 68.

In another aspect, the present invention comprises a surgical instrument that includes a means to allow for visualization of a drug or the needle used to administer the drug that is injected into target tissue such as the prostate gland. The invention can be divided into categories of ways to make the needle more visible on ultrasound and ways to make the fluid delivered more visible.

Figure 6:
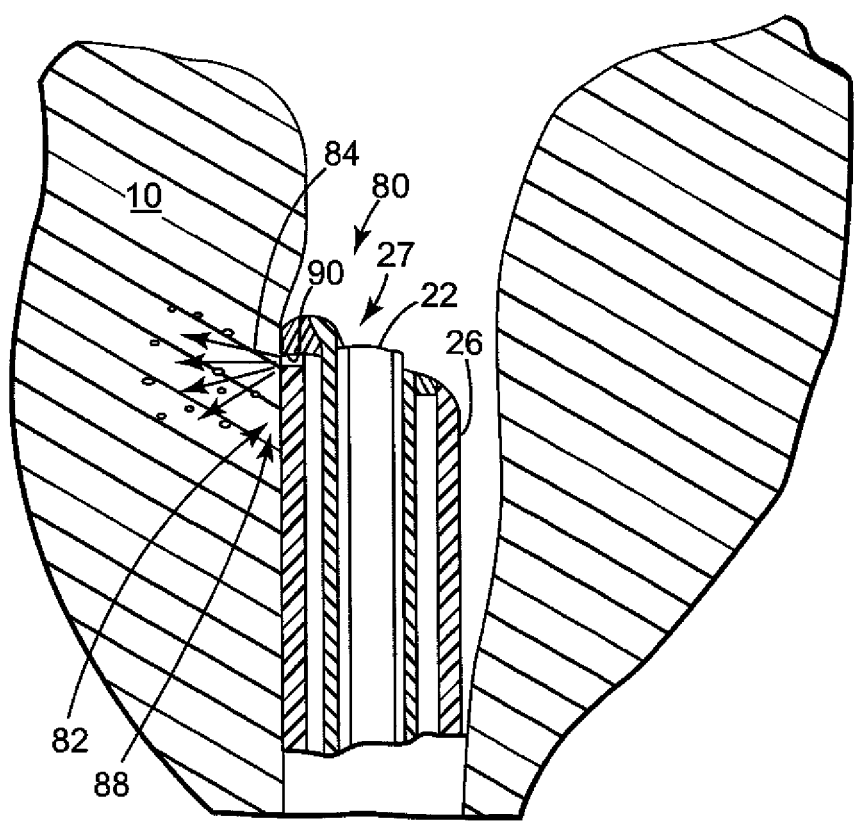
FIG. 6 is a high pressure transurethral drug delivery embodiment of the present invention.
Figure 7:
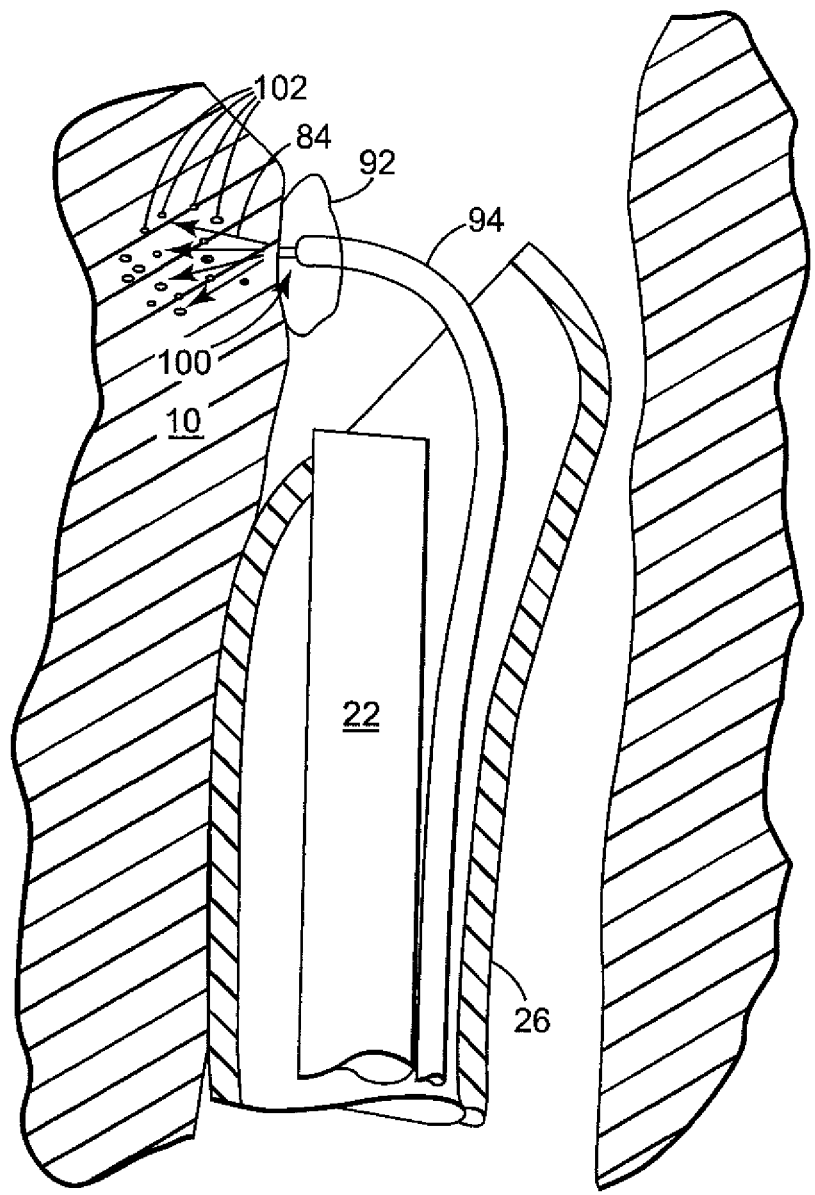
FIG. 7 is another variation of the embodiment of FIG. 6 to illustrate an additional surgical instrument and method according to the present invention.
Figure 8:
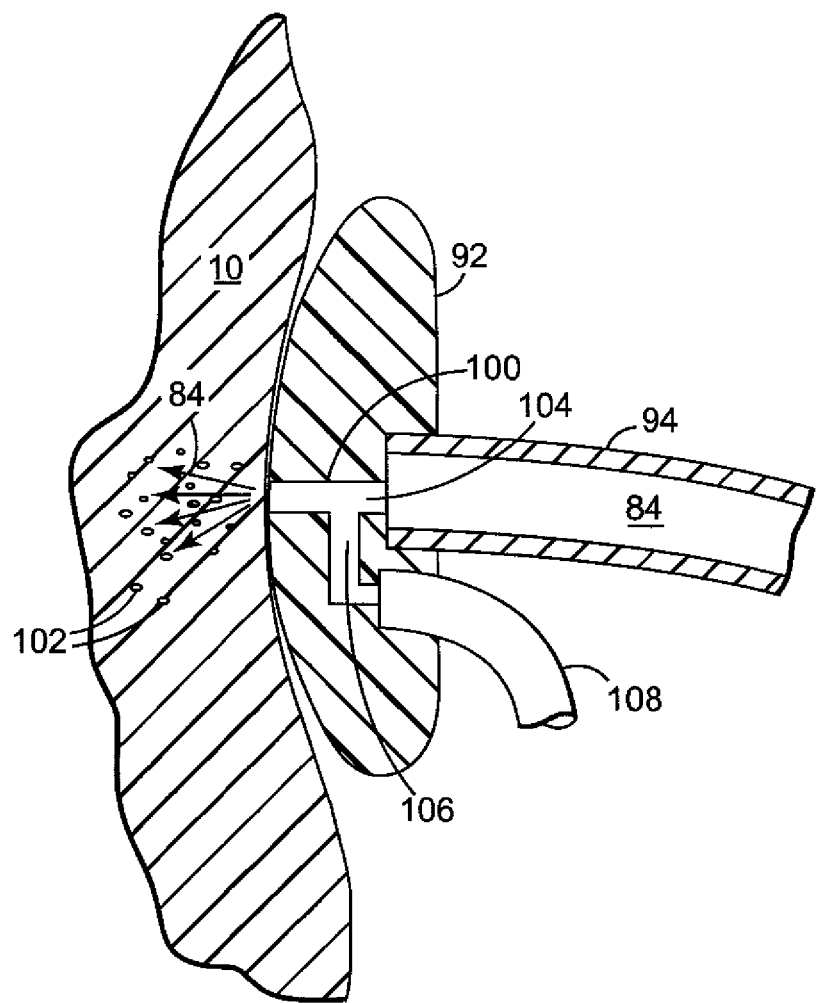
FIG. 8 is an enlarged view of a portion of FIG. 7.

Another aspect of the present invention is shown in FIGS. 6 through 8. In this aspect, the present invention comprises a method with the step of injecting a drug into the prostate using a high-pressure needle-less injection system 80. A novel device 82 forms an aspect of the present invention and can operate independently or with a cystoscope 27 for transurethral delivery of ethanol 84 into the prostate 10. Advantages over a needle delivery system could include better depth of penetration control, containment within the prostate capsule, better volume delivery (minimize extravasation), faster procedure, less pain, and possible bubble formation or bubble injection for visualization in TRUS (transrectal ultrasound). As an alternative, an echogenic substance can be added to the ethanol to enable visualization during the procedure to assess penetration depth.

In FIG. 6, ethanol 84 is injected into the prostate 10 by high pressure needle-less means 88, preferably in the form of an aperture 90 delivering high pressure ethanol to a site adjacent the prostate transurethrally. This would have the advantages mentioned over a needle system and would be expected to further include better depth of ethanol penetration control. Optionally, a balloon may be used to press the means 88 against urethral tissue to ensure suitable contact between the means 88 and the urethral tissue.

FIG. 7 shows a variation of this approach in which a clear plastic or polymer injection head 92 located adjacent a portion of the prostate 10. A high pressure fluid delivery tube 94 is connected to head 92. Borescope 22 is located within the cystoscope sheath 26 along with tube 94. In operation, head 92 is positioned as desired using the borescope 22 for visual observation while manipulating the sheath 26. A nozzle 100 delivers high pressure ethanol 84, with echogenic bubbles 102, if desired. Optionally, a visually perceptible marker may be placed on or in the head 92 to indicate its position. A urethral balloon may also be used with this embodiment of the present invention.

Referring now also to FIG. 8, an enlarged view of the injection head 92 may be seen. In this view, it may be seen that the nozzle 100 has a first inlet 104 connected to tube 94 for delivering a chemical agent such as ethanol under high pressure. Nozzle 100 also has a second inlet 106 connected to a gas delivery tube 108 for introducing pressurized gas to form bubbles 102 as an echogenic agent in the prostate tissue 10.

Figure 9:
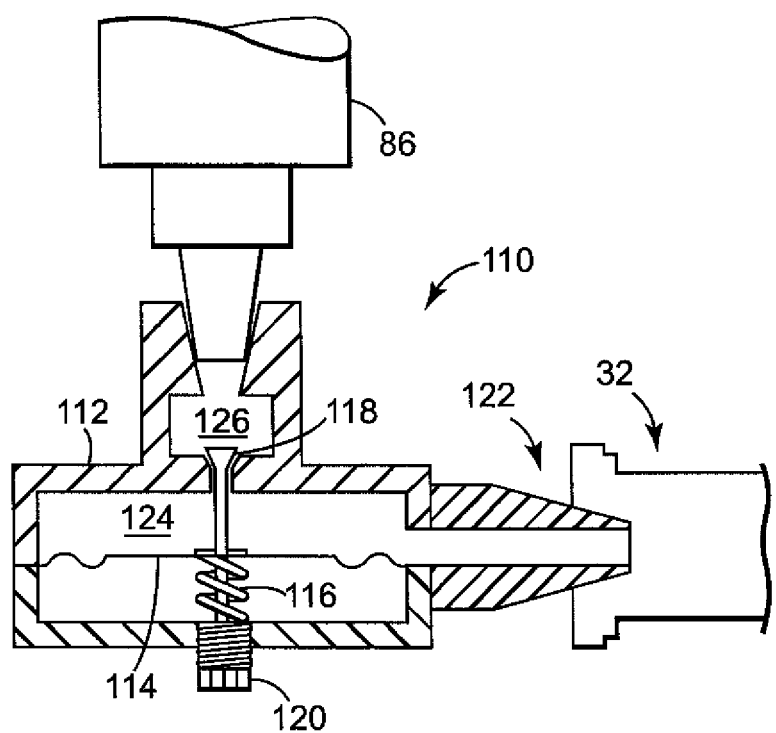
FIG. 9 is a view of an additional feature of the surgical instrument and method according to the present invention.
Figure 10:
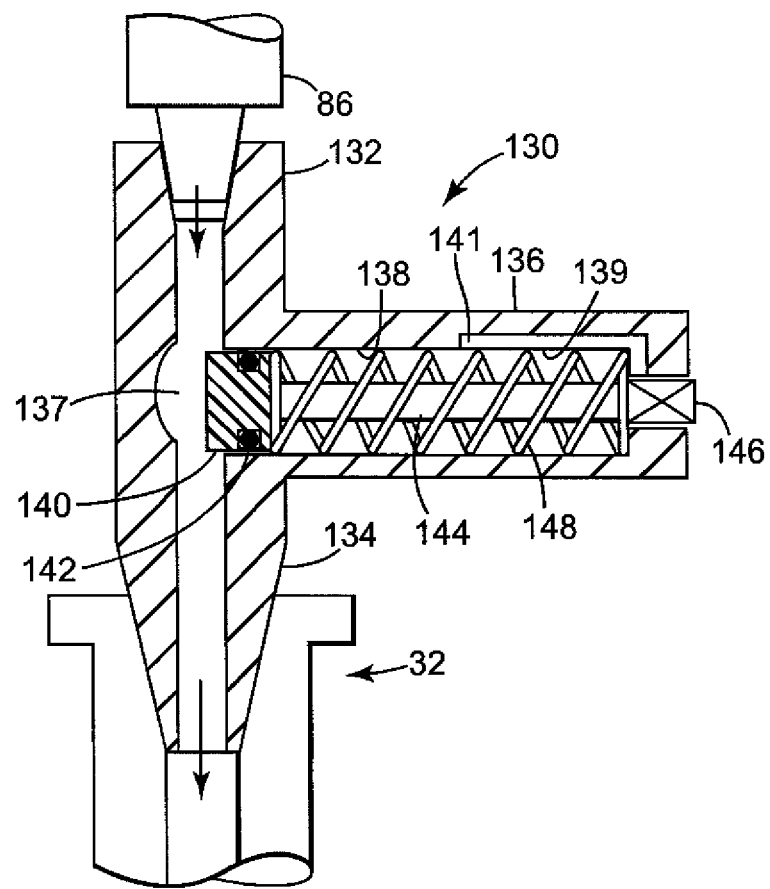
FIG. 10 is a view of still another feature of the surgical instrument and method according to the present invention.

FIGS. 9 and 10 illustrate other aspects of the present invention. These aspects of the surgical instrument 20 include means to either limit injection pressures to predetermined or desired levels during a transurethral ablation of the prostate (TEAP) procedure or features to indicate when unacceptably high pressures are reached.

FIG. 9 is a pressure limiter 110 for ethanol injection. A Luer-Lok® type syringe 86 is connected to a housing 112 containing a pressure sensing diaphragm 114, biased by a spring 116 to hold a shut-off valve 118 in an open position as shown. An (optional) adjustment screw 120 may be used to set the pressure at which valve 118 closes. The output 122 of the pressure limiter 110 is connected to the ethanol syringe port 32 of the Prostaject device 50. The in-line pressure limiting valve can be used to prevent injection pressures from exceeding acceptable levels during TEAP procedures. If pressures become excessive at the injection site, extravasation can result or rapid flow can occur along tissue planes that allows the ethanol to miss the intended target. In operation, when the force resulting from pressure inside housing 112 in chamber 124 exerted on diaphragm 114 exceeds the force resulting from spring 116, diaphragm 114 will move towards screw 120, closing valve 118. Valve 118 will remain closed for as long as sufficient pressure exists in chamber 126 to cause a force on valve 118 to remain closed against the force of spring 116. Once the pressure in chamber 126 is reduced, the force from spring 116 will open valve 118, and allow fluid to flow from chamber 126 to chamber 124 and outlet 122.

Referring now to FIG. 10, a pressure indicator 130 may be seen. Indicator assembly 130 preferably has an inlet fitting 132 for receiving a Luer Lok® syringe 86 and an outlet fitting 134 for coupling to the Luer Lok® compatible ethanol syringe port 32 on an Prostaject device 50. It is to be understood that fittings 132 and 134 are shown in simplified form, without Luer Lok® details. Inlet and outlet fittings 132, 134 are preferably formed integrally with a housing 136 which defines a passage 137 connecting inlet 132 to outlet 134. Housing 136 further includes a cylinder 138 carrying a piston 140 having an O-ring seal 142 sealing the piston 140 against the cylinder 138. Piston 140 also has a rod or stem 144 carrying a visually perceptible indicator or flag 146 at a distal end thereof. Indicator housing 136 also contains a spring 148 urging piston 140 to a retracted position, shown in solid lines in FIG. 10, in which flag 146 is concealed within housing 136. In operation, as pressures reach unacceptable levels (e.g., during a TEAP procedure), the moving rod 144 will extend, working against the preset force of spring 148. The flag 146 will then extend beyond housing 134, and indicate to the physician that pressures have exceeded acceptable levels. A groove 139 extends part way along the cylinder 138 in housing 136 to allow fluid to bleed past the piston and O-ring seal 142 in the event a predetermined maximum pressure level is reached. The groove 139 begins at a starting point 141 and extends a distance along the cylinder such that the liquid drug will leak past the piston 140 and O-ring seal 142 via the groove 139 when a predetermined maximum pressure level is reached within the passage 137 causing the piston 140 to move against the spring 148 a distance sufficient to move the piston past the starting point 141 of the groove 139.

Figure 11:
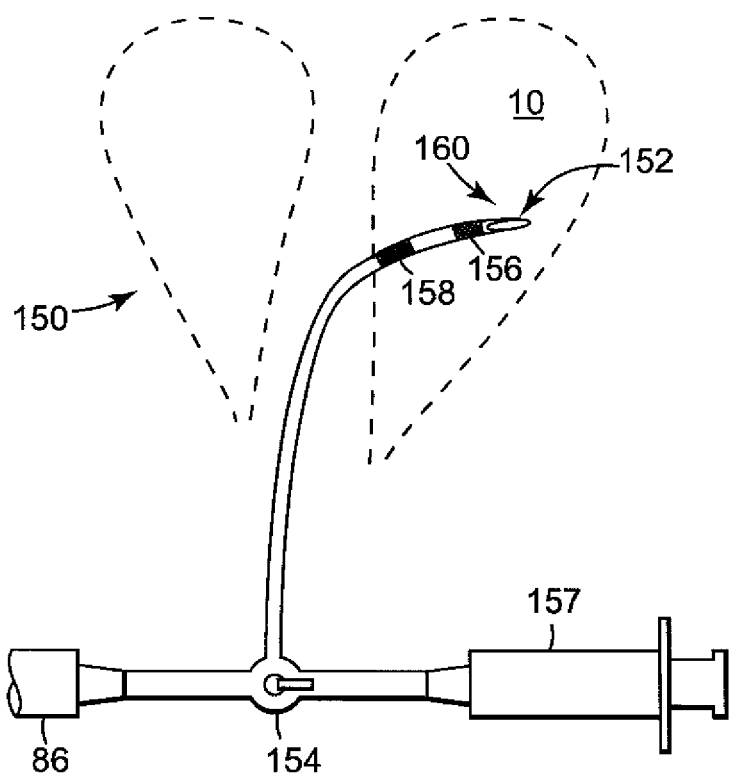
FIG. 11 is a view of an arrangement to switch between ethanol and an echogenic agent useful in the practice of the present invention.
Figure 12A:
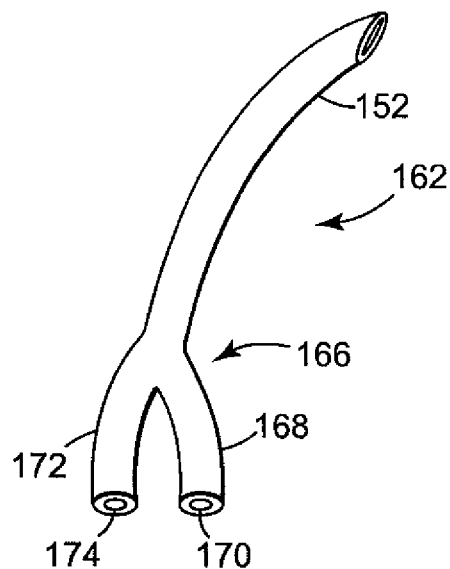
FIG. 12a is a perspective view of an alternative embodiment of the surgical instrument and method of the present invention.
Figure 12B:
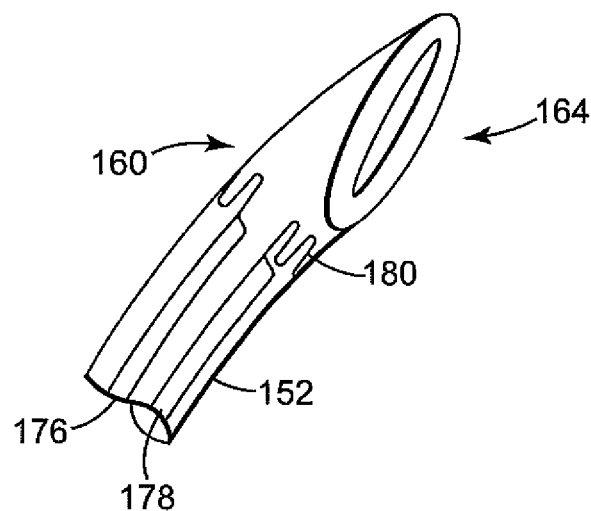

FIGS. 11, 12a and 12b illustrate additional aspects of the surgical instrument and method according to the present invention. These aspects include means for making the needle more visible including the following. 1) The needle can be sandblasted to improve the ability to identify its location via ultrasound. 2) The needle can have a thin film conductor deposited over a dielectric for the purpose of operating a resistor for generating heat or a piezoelectric driver for generating ultrasonic vibration that could be detected via ultrasound imaging. The dielectric capacitance and length of strip create a L-C monopole or bipolar antenna emitting a frequency spectrum to be picked up by external receiver and/or alternatively by ultrasound probe. 3) Echogenic materials could be injected after the needle is inserted into the prostate to verify needle position via TRUS. The ethanol (or other drug) could then be injected. The echogenic materials could include microspheres in a fluid medium, gas bubbles or solid particles suspended in solutions. 4) The echogenic materials could be added to the drug and injected simultaneously either through mixing them before injection or using a double-barreled syringe and having them mix in the needle as seen in FIG. 11.

Notably, the surgical device may optionally include an ultrasonic transducer (e.g. on or near the needle), to enhance the dispersion of the injected substance within the tissue. In another embodiment, the surgical needle may include a coating (e.g. on the needle) of Echo-Coat® material (available from STS Biopolymers Inc.) for better visualization and control.

FIG. 11 shows a simplified view of an ethanol injection visualization 150 with a number of parts of the surgical instrument 20 omitted for simplicity. In this visualization, a cannula 152 is connected to a manual device or valve 154 for switching between an echogenic agent and the ethanol. One or more sand blasted surfaces in the form of bands 156, 158 are located at a distal end 160 of the cannula 152 in order to identify the needle tip and/or the location of injection of ethanol into the prostate 10. Several means can be employed: 1) The drawing of FIG. 11 shows a two-syringe system that could inject an agent visible on ultrasound first using the echogenic agent syringe 157, then inject the ethanol using the ethanol syringe 86 after the position has been identified. The echogenic agent could include microspheres, solid particles in suspension, bubbles, fluids different in density from water, etc. 2) The needle itself can be modified to have better visualization on ultrasound. One way to accomplish this is to roughen the surface of the needle using sandblasting (as shown in FIG. 11) or other means, as illustrated in FIG. 12b.

FIGS. 12a and 12b show further ethanol injection visualizations 162, 164. FIG. 12a illustrates a means to inject a drug (ethanol) in combination with an echogenic marker or radio-opaque marker simultaneously using a Y-connection 166 where the fluids mix, coming from a first tube 168 having a lumen 170 carrying the ethanol and a second tube 172 having a lumen 174 carrying the echogenic agent, both of which are connected via the Y-connection 166 to the cannula 152. FIG. 12b illustrates an alternative embodiment of cannula 152 having first and second thin film conductors 176, 178 connected near the distal end 160 of cannula 152 to a resistor 180 or thin film/MEMS to produce a temperature signal or a piezo oscillator to produce an ultrasonic beacon.

FIGS. 13a through 15b are views of additional embodiments of surgical instruments and methods according to the present invention. These embodiments have a mechanism for raising the needle 25 in a perpendicular or substantially perpendicular fashion relative to the sides of a needle deployment port. Optionally, an infrared or other light spot may be projected perpendicular to the sheath to the location in the body that would receive the needle. This feature would allow the surgeon to presight or target the specific tissue to be treated.

FIGS. 13a, 13b, 13c, 13d, 14a, 14b, 15a and 15b show various embodiments of the present invention which have structure for raising the needle in perpendicular or substantially perpendicular direction to the longitudinal axis of the device. Moving the needle in this fashion is believed to provide better control over placement of the needle and thus, the injectable substance. Assemblies for raising a structure in a direction that is perpendicular or substantially perpendicular to the longitudinal axis of a surgical device are described in U.S. Pat. No. 5,306,284 to Agee et al., the contents of which are incorporated herein by reference.

Figure 13A:
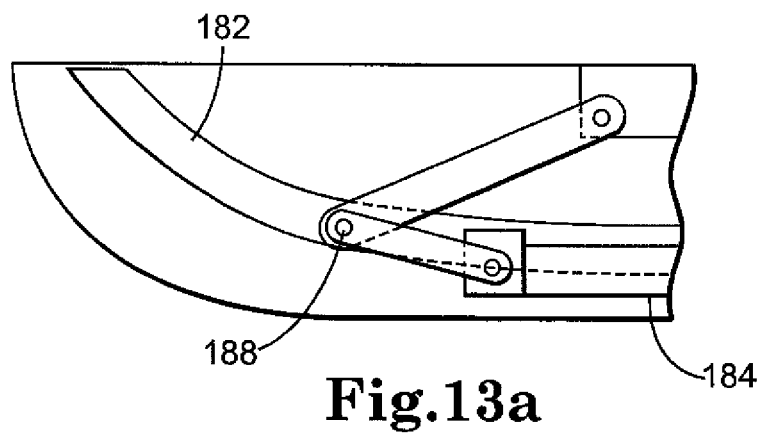
FIG. 13a is a view of an alternative embodiment of a surgical instrument in a first position according to the present invention.
Figure 13B:
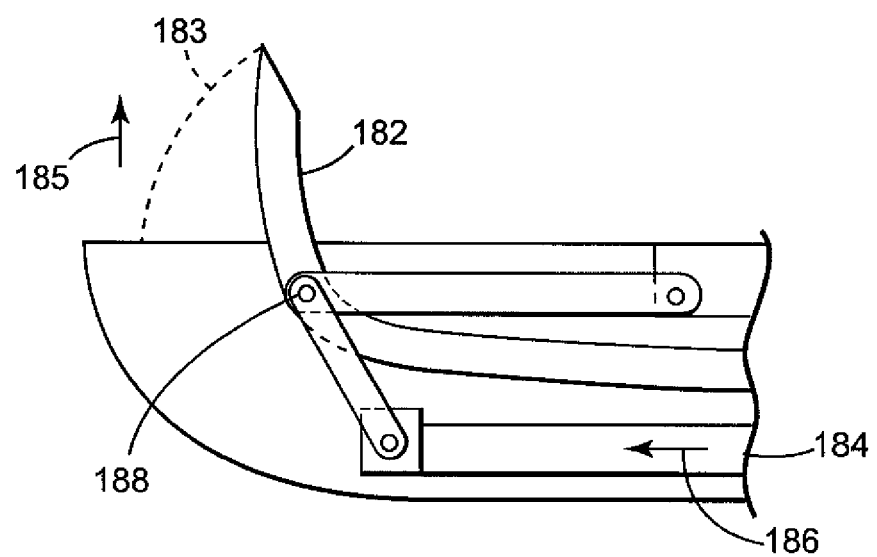
FIG. 13b is a view of the embodiment of FIG. 13a in a second position.
Figure 13C:
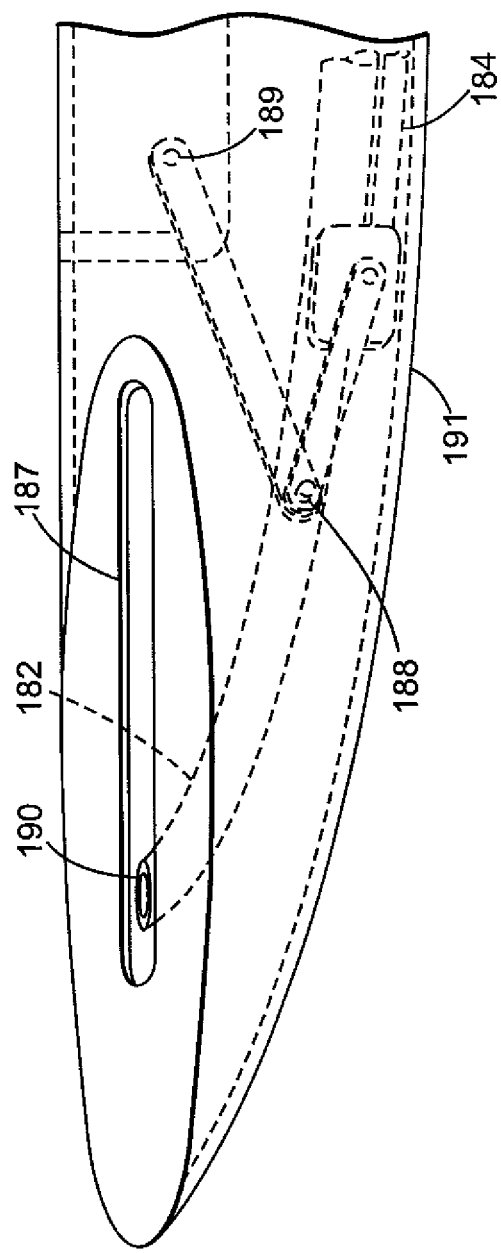
Figure 13D:
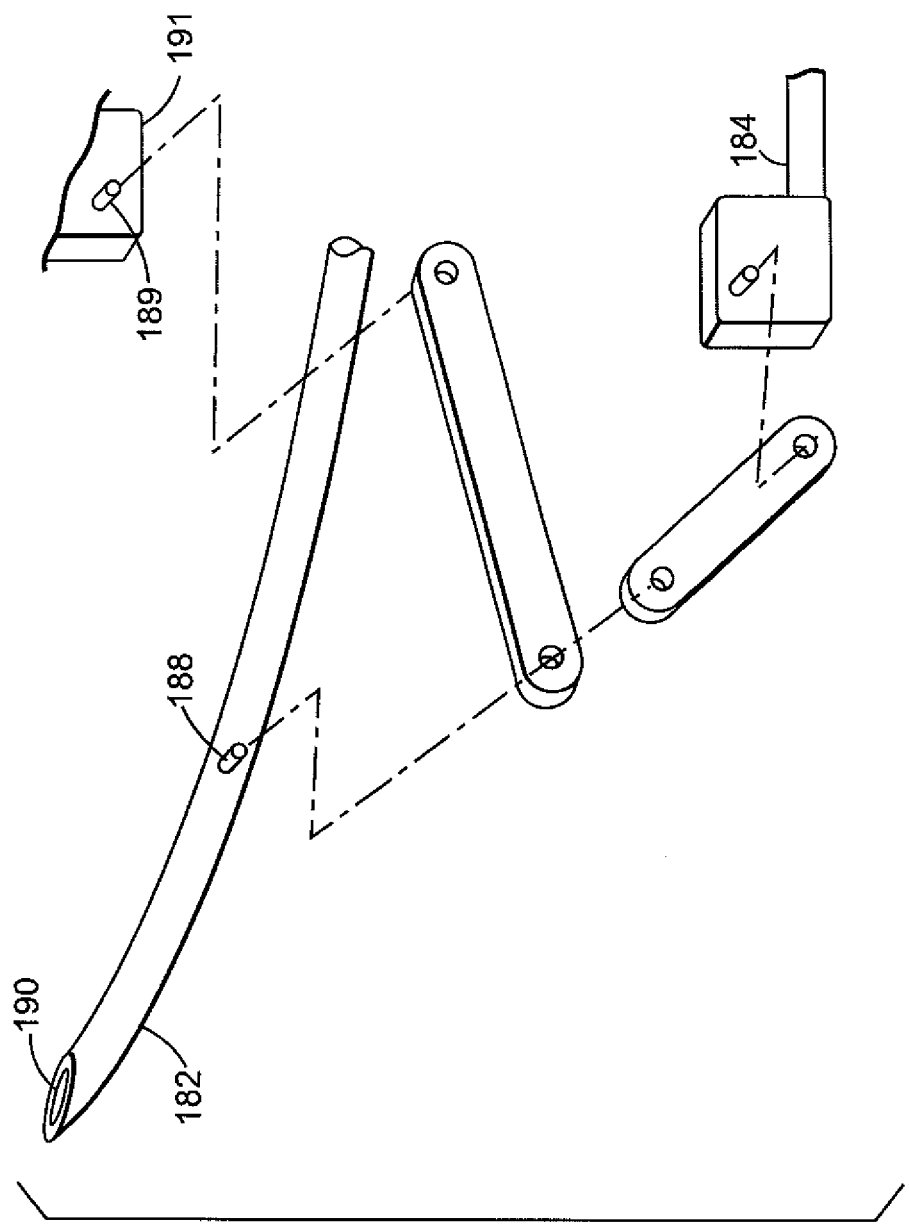
FIG. 13d is an exploded view of the embodiment of FIG. 13c.
Figure 14A:
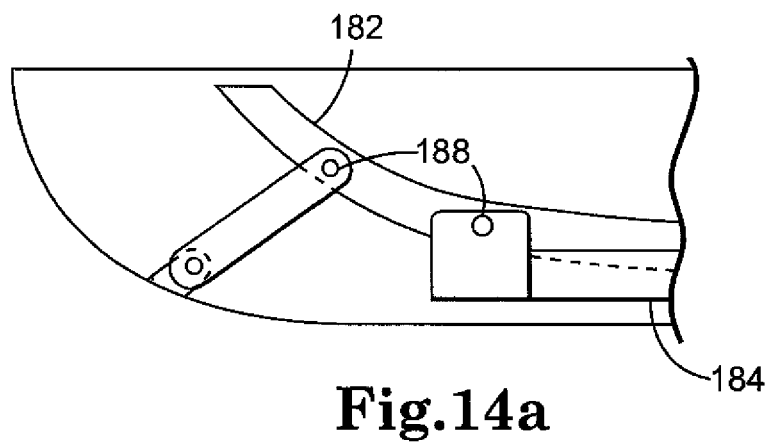
FIG. 14a is a view of an alternative embodiment of a surgical instrument in a first position according to the present invention.
Figure 14B:
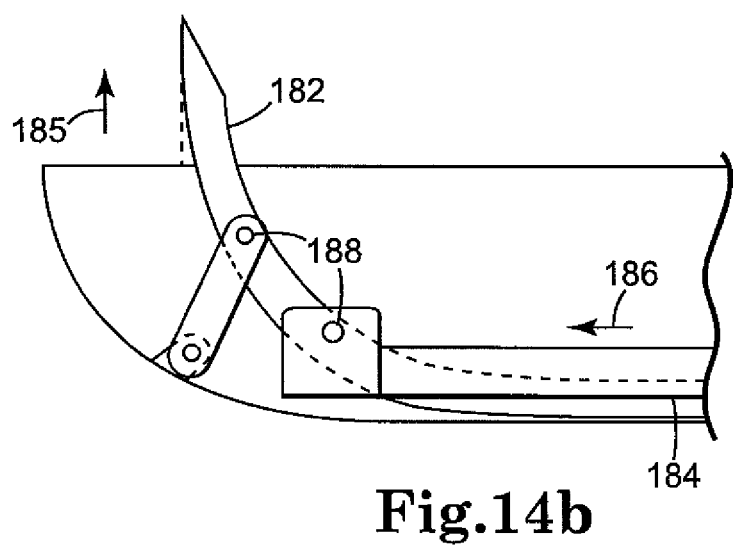
FIG. 14b is a view of the embodiment of FIG. 14a in a second position.
Figure 15A:
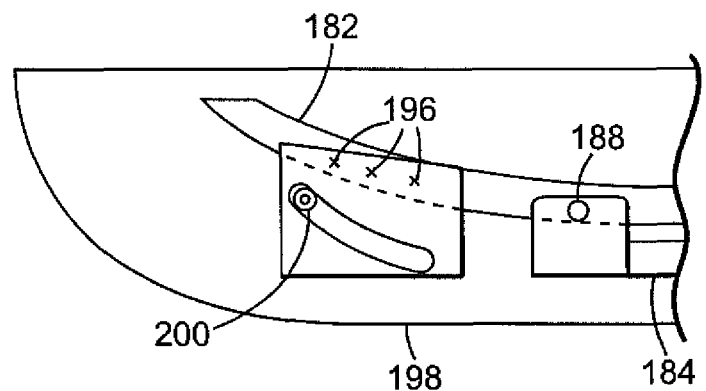
FIG. 15a is a view of an alternative embodiment of a surgical instrument in a first position according to the present invention.
Figure 15B:
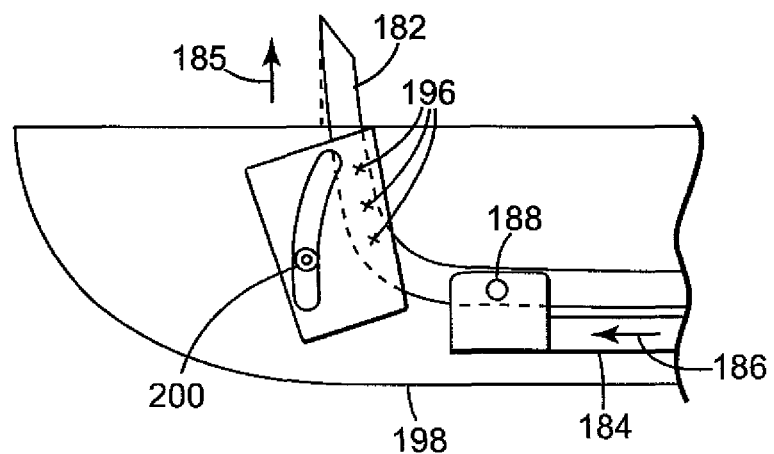
FIG. 15b is a view of the embodiment of FIG. 15a in a second position.

FIGS. 13a and 13b illustrate an embodiment having needle 182 operated by a pusher 184, which moves in the direction of arrow 186 to raise the needle 182 along path 183 and in the general direction of arrow 185. FIG. 13c is a perspective view corresponding to FIG. 13a, and FIG. 13d is an exploded view of this embodiment. It is to be understood that one or more trunnions 188 project out from needle 182 without blocking or providing a leak path with respect to the lumen 190 interior of needle 182. In FIGS. 13c and 13d it is to be understood that pivot pill 189 is secured to a housing 191 of the assembly. In FIG. 13c the needle 182 is guided by a slot 187 to avoid urethral damage that might otherwise occur due to excessive needle displacement. Furthermore, such a slot guide is expected to reduce the potential for high backflow due to low resistance with an enlarged opening that could reduce the effectiveness of the treatment using the apparatus or method of the present invention. FIGS. 14a and 14b illustrate another embodiment having needle 182 operated by pusher 184, with at least two trunnions 188 on needle 182. Pusher 184 is moved in the direction of arrow 186 to raise needle 182 generally in the direction of arrow 185. FIGS. 15a and 15b illustrate still another embodiment having needle 182 operated by pusher 184 via trunnion 188 on needle 182. Pusher 184 is pushed in the direction of arrow 186 to raise needle 182 generally in the direction of arrow 185. In this embodiment, a plate 192 having a curved slot 194 is fastened to needle 182 by conventional means such as welding 196. Slot 194 acts against a roller 196 secured to housing 198 to cause needle 182 to move in response to movement of pusher 184.

Figure 17:
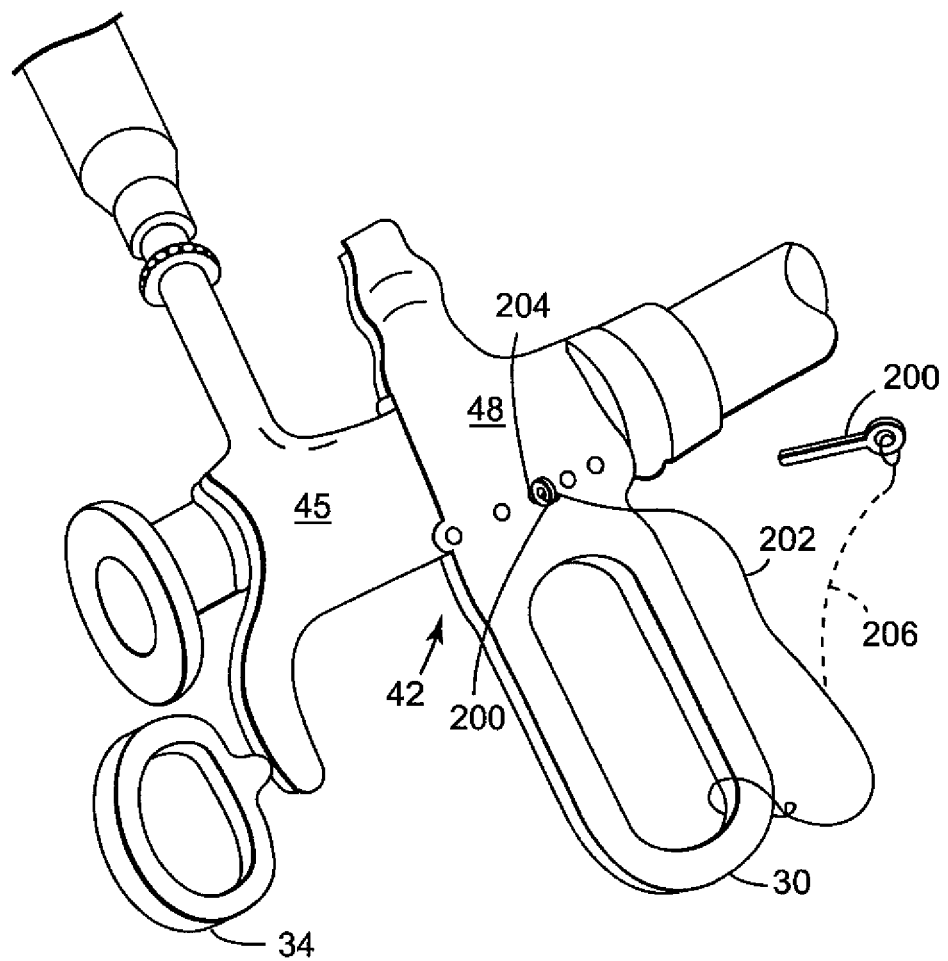
FIG. 17 is a fragmentary view of the surgical instrument showing an alternative embodiment of a locking mechanism useful in the practice of the present invention.

Referring now to FIG. 17, a still further variation of a lockout release 42 may be seen. In this variation, a loose pin 200 (preferably retained by a tether 202) is inserted manually into one of a plurality of pairs of through apertures 204 present for the detents 28 in the Prostaject device 50. Placing the pin 200 in an aligned aperture pair 204 prevents advancement of the slide 45 associated with thumb ring 34 past a desired detent position with respect to frame 48 associated with handle 30, and thus prevents over advancing needle 25 from the needle deployment port 24. It is to be understood that FIG. 17 shows pin 200 in both an installed position in aperture 204, and in a free position, with the tether indicated by dashed line 206 in the free position. It is to be further understood that the apertures corresponding to predetermined distances the needle may be extended correspond to the various detent positions. In operation, the slide will be released to advance until an edge of the structure of the slide contacts the pin in one of the apertures 204, limiting the movement of the slide with respect to the frame, as desired. A further variation of this approach is to provide an aperture which prevents any extension of the needle with the pin received in the aligned aperture pair, with one aperture in the slide and the other aperture in the frame.

Figure 18A:
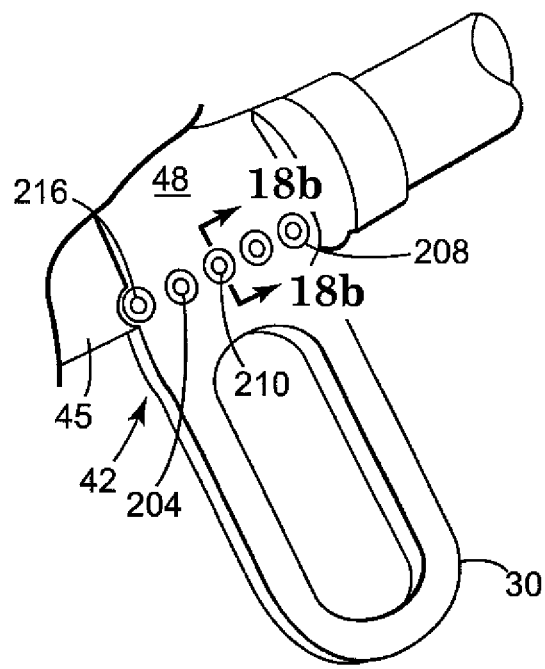
FIG. 18a is fragmentary view of the surgical instrument showing an alternative embodiment of a locking mechanism useful in the practice of the present invention.
Figure 18B:
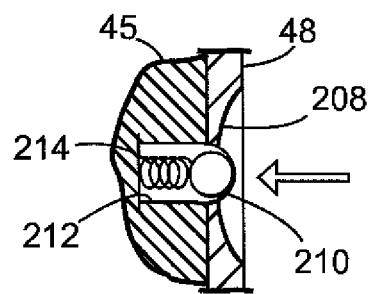

FIG. 18a is a fragmentary view and FIG. 18b is a partial section view (along line 18b-18b of FIG. 18a) of yet another variation of the lockout release 42. In this variation, each detent 28 is surrounded by a generally spherical recess 208. In this variation, a ball 210 of the detent 28 projects sufficiently far out of a recess 212 in slide 45 to block transverse movement of slide 45 with respect to frame 48. When it is desired to permit transverse movement of slide 45 with respect to frame 48 (to advance or retract needle 25) ball 210 is manually depressed into recess 212 by engagement of an operator's finger in the spherical recess 208. A spring 214 urges ball 210 away from recess 212. It is to be understood that the frame 48 of the handle 30 of the Prostaject device 50 currently has the ball 210 that fit into the holes 204 to indicate position and act as detents 28 because the ball 210 only rests partially in one of holes 204. This currently gives slight resistance to movement. If the ball 210 and hole diameter are sized to give a positive lock, that cannot be overcome by just the pressure on the thumb ring 34 pushing the slide 45 forward toward the handle 30. in one form of this variation, only the back hole 216 can be made such that a finger of the operator's hand can push the ball 210 in and release the lock in the hole 216, while the other holes 204 can be sized to give only slight interference.

Figure 19B:
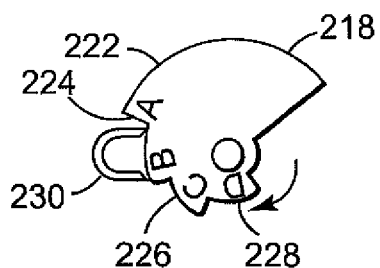
Figure 19A:
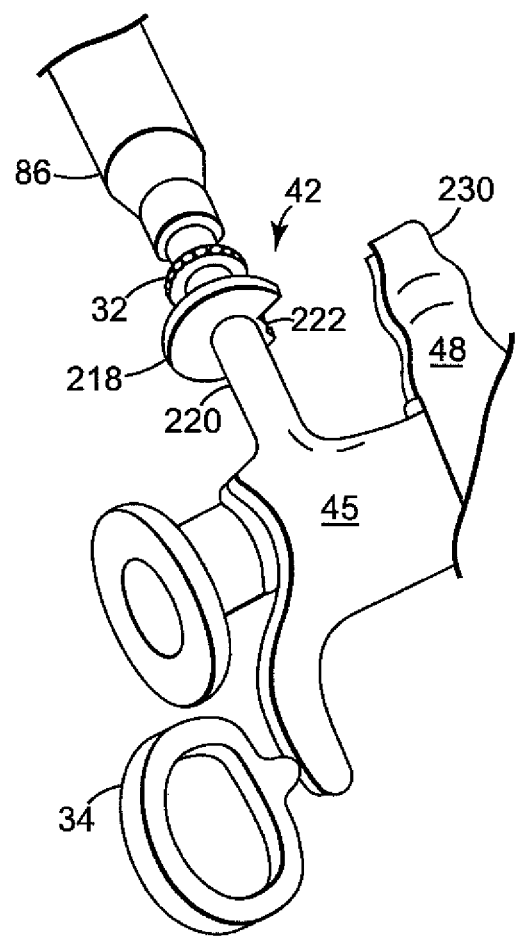
FIG. 19a is a fragmentary view of the surgical instrument showing a still further alternative embodiment of a locking mechanism useful in the practice of the present invention.

Referring now to FIGS. 19a and 19b, a stepped cam version of the lockout release 42 is shown. In this version a stepped cam 218 is located for rotational movement on the projection 220 that carries the ethanol syringe port 32. The stepped cam 218 is in the form of a disk having steps 222, 224, 226, and 228 with different radii and individual indices, represented by the letters "A" "B" "C" and "D." It is to be understood that the projection 220 moves forward to the top finger support 230 where the cam 218 will hold the slide and frame apart by the distance set by the respective radius selected on cam 218 to be positioned between the projection 220 and finger support 230. In operation, when the physician is ready to advance the needle 25 out from port 24, he or she would rotate the disk 218 to a position that allows the needle 25 to be advanced to a predetermined distance. The physician would then advance the thumb ring 34 toward handle 30, moving needle 25 forward until the selected step on disk 218 bottoms out against finger support 230. It is to be understood that the indices associated with the steps preferably indicate the respective distances of advance for the needle 25.

Figure 20:
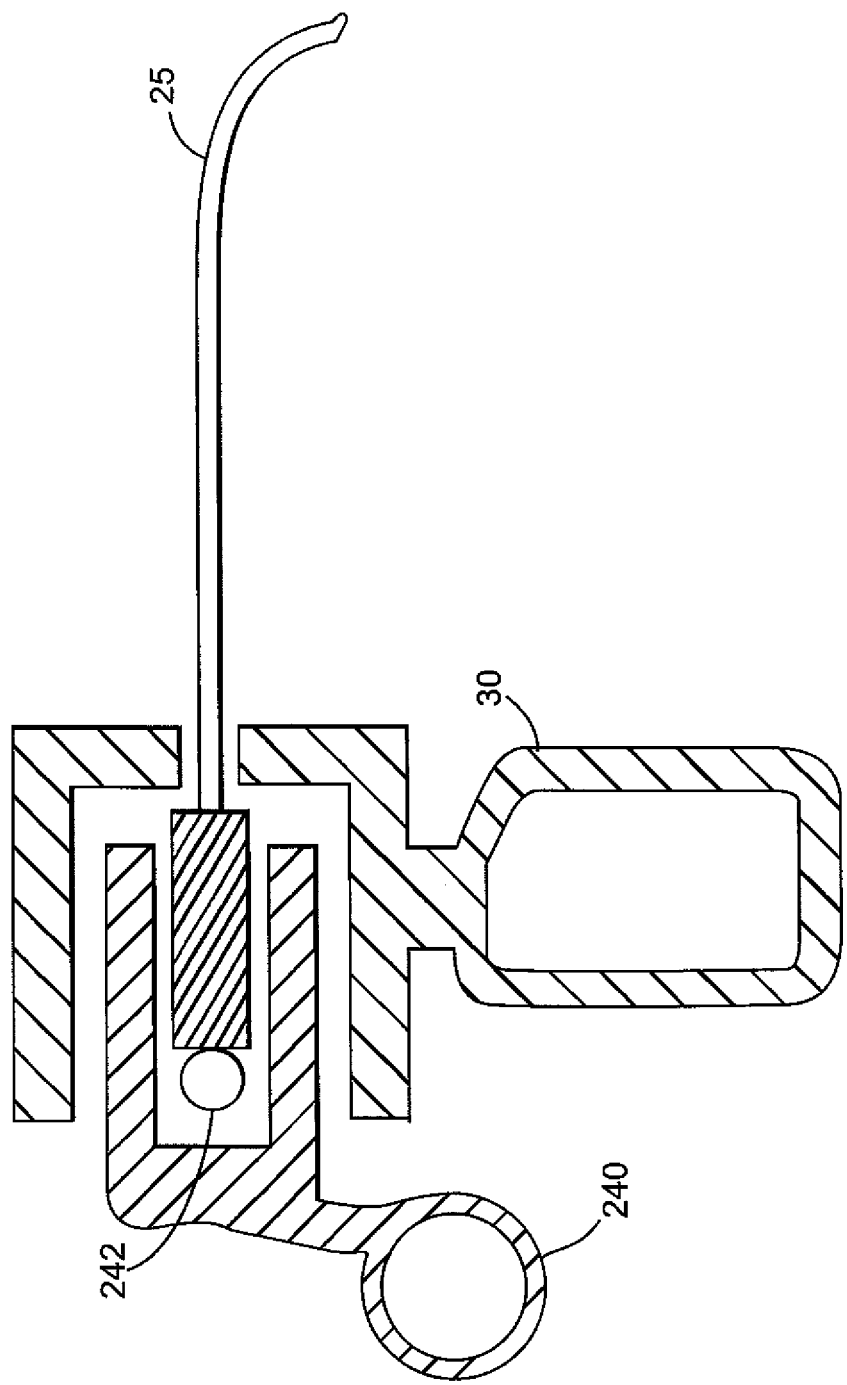
FIG. 20 is a fragmentary section view of an alternative embodiment of a de-coupling mechanism useful in the practice of the present invention.

Referring now to FIG. 20, a de-coupling mechanism useful in the practice of the present invention may be seen. In this version, a switch 242 provides for de-coupling a handle 240 from the needle 25 to prevent unwanted needle extension instead of blocking relative movement of the two members as described for the embodiment of, e.g., FIG. 5. This allows the handle 240 to slide back and forth without movement of the needle until the switch or button 242 is pushed (or other actuation is used) that re-couples the handle 240 to the needle 25 and then allows the needle 25 to be advanced with the handle 240. Specifically, in FIG. 20, the handle 240 (corresponding to thumb ring 34) is able to move relative to the needle 25 without button 242 being pushed. When button 242 is pushed, the handle 240 is mechanically connected to the needle 25 to advance and retract the needle, by movement of the handle 240 with respect to handle or finger grip 30. It may thus be seen that the embodiment of FIG. 20 provides selective coupling apparatus for a surgical instrument of the type having an remotely controllable extendable and retractable needle. The selective coupling apparatus includes a mechanism for selectively engaging and releasing first and second members (such as handles 240 and 30) from moving with respect to each other. The mechanism provides a mechanical connection between the first and second members when in an operating condition (when button 242 is pushed) and the mechanism provides clearance between the first and second members when in a de-coupled condition (when button 242 is released).

In describing preferred embodiments of the invention, specific terminology is used for the sake of clarity. The invention, however, is not intended to be limited to the specific terms so selected, and it is to be understood that each term so selected includes all technical equivalents that operate similarly.

These and other advantages of the invention are more fully shown and described in the drawings and detailed description of this invention, where like reference numerals are used to represent similar parts. It is to be understood, however, that the drawings and description are for the purposes of illustration only and should not be read in a manner that would unduly limit the scope of this invention. This invention may take on various modifications and alterations without departing from the spirit and scope thereof.

What is claimed is:

1. A method of injecting a drug into urethral tissue, comprising the steps of:
    positioning a distal end of a needleless injector adjacent a region of urethral tissue into which it is desired to inject the drug, the injector comprising at least one injection orifice at a distal end of a shaft and an expandable balloon operatively positioned relative to the at least one injection orifice;
    inflating the balloon until the at least one injection orifice is pressed against the urethral tissue and a desired amount of contact is achieved between the at least one injection orifice and the urethral tissue; and
    ejecting a high pressure stream of the drug from the at least one injection orifice into the urethral tissue.

2. The method of claim 1, wherein the drug ejected from the at least one injection orifice is a fluid.

3. The method of claim 2, wherein the fluid comprises high-pressure ethanol.

4. The method of claim 1, wherein the step of ejecting the drug further comprises ejecting echogenic bubbles with the drug.

5. The method of claim 1, further comprising the step of deflating the balloon after a desired quantity of the drug is ejected into the urethral tissue.

6. The method of claim 1, wherein the needleless injector further comprises:
    a body at a proximal end, wherein the shaft extends distally from the body;

a fluid chamber at the proximal end, wherein the fluid chamber is in fluid communication with the at least one injection orifice; and a pressure source in communication with the fluid chamber;

wherein the step of positioning the distal end of the injector relative to urethral tissue comprises positioning the distal end of the injector in a location so that when the balloon is inflated, the urethral tissue is tensioned at a location for injection of fluid from the at least one injection orifice into the urethral tissue.

7. The method of claim 1, wherein the step of ejecting the drug into the urethral tissue comprises ejecting the drug from the at least one injection orifice in a direction that is generally parallel to a longitudinal axis of the at least one injection orifice.

8. The method of claim 1, wherein the needleless injector further comprises a cystoscope operatively positioned relative to the at least one injection orifice.

9. The method of claim 1, wherein the step of ejecting a high pressure stream of the drug further comprises ejecting the drug into prostate tissue.

10. The method of claim 9, wherein the step of ejecting a high pressure stream of the drug comprises delivering the drug transurethrally to the prostate tissue.

* * * * *